United States Patent
Sakurai et al.

(10) Patent No.: US 10,391,119 B2
(45) Date of Patent: Aug. 27, 2019

(54) LACRIMAL OILY LAYER STABILIZER AND EYE DROPS COMPRISING SAME

(71) Applicant: NOF CORPORATION, Shibuya-ku, Tokyo (JP)

(72) Inventors: Shunsuke Sakurai, Kawasaki (JP); Koji Miyamoto, Kawasaki (JP); Yoshihisa Shimamura, Kawasaki (JP); Nobuyuki Yamamoto, Kawasaki (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 16/061,839

(22) PCT Filed: Dec. 21, 2016

(86) PCT No.: PCT/JP2016/088094
§ 371 (c)(1),
(2) Date: Jun. 13, 2018

(87) PCT Pub. No.: WO2017/110874
PCT Pub. Date: Jun. 29, 2017

(65) Prior Publication Data
US 2018/0360872 A1    Dec. 20, 2018

(30) Foreign Application Priority Data

Dec. 22, 2015 (JP) ................................. 2015-250710

(51) Int. Cl.
*A61K 31/78* (2006.01)
*A61P 27/04* (2006.01)
*A61K 31/80* (2006.01)
*A61K 9/00* (2006.01)

(52) U.S. Cl.
CPC ............ *A61K 31/80* (2013.01); *A61K 9/0048* (2013.01); *A61K 31/78* (2013.01)

(58) Field of Classification Search
None
See application file for complete search history.

(56) References Cited

U.S. PATENT DOCUMENTS

2008/0051741 A1* 2/2008 Grenon ...................... A61F 9/00
                                                                 604/290
2016/0199526 A1* 7/2016 Sakurai ................ A61K 9/0048
                                                                 514/635

FOREIGN PATENT DOCUMENTS

| JP | H10-324634 | * 12/1998 | ............. A61K 31/80 |
| JP | 2008-273959 | 11/2008 | |
| JP | 2011-75943 | 4/2011 | |
| WO | 99/26637 A1 | 6/1999 | |
| WO | WO 2015/029717 | * 3/2015 | ............. A61K 47/38 |

OTHER PUBLICATIONS

PCT International Search Report dated Jan. 31, 2017 in connection with PCT International Application No. PCT/JP2016/088094, 3 pages.

* cited by examiner

*Primary Examiner* — Brian Gulledge
(74) *Attorney, Agent, or Firm* — Amster, Rothstein & Ebenstein LLP

(57) ABSTRACT

Provided is a tear lipid layer stabilizer that is capable of stabilizing a tear lipid layer and allowing the tear lipid layer to sufficiently spread over a corneal surface, to thereby prevent the evaporation of a tear aqueous layer on the corneal surface, and hence is suitable for amelioration, alleviation, or treatment of evaporative dry eye symptoms caused by Meibomian gland dysfunction, an ophthalmic solution having blended therein the tear lipid layer stabilizer, and a tear lipid layer-stabilizing method using the tear lipid layer stabilizer. The tear lipid layer stabilizer includes a copolymer that has a weight-average molecular weight of from 10,000 to 5,000,000, and contains 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer.

8 Claims, 1 Drawing Sheet

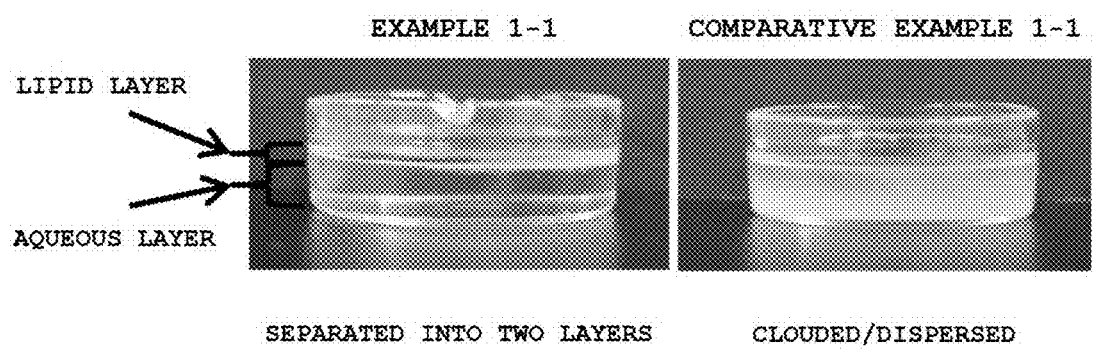

LACRIMAL OILY LAYER STABILIZER AND EYE DROPS COMPRISING SAME

CROSS-REFERENCE TO RELATED APPLICATIONS

This application is a U.S. national stage entry under 35 U.S.C. § 371 of PCT International Patent Application No. PCT/JP2016/088094, filed Dec. 21, 2016, which claims priority to Japanese Patent Application No. 2015-250710, filed Dec. 22, 2015, the contents of which are incorporated by reference herein into the subject application.

TECHNICAL FIELD

The present invention relates to a tear lipid layer stabilizer using a copolymer containing a constituent unit based on 2-(meth)acryloyloxyethyl phosphorylcholine and a constituent unit based on an alkyl group-containing (meth)acrylic monomer, and to an ophthalmic solution containing the same. More specifically, the present invention relates to an ophthalmic solution for prevention, alleviation, amelioration, or treatment of evaporative dry eye symptoms caused by Meibomian gland dysfunction.

The present application claims priority from Japanese Patent Application No. 2015-250710, which is incorporated herein by reference.

BACKGROUND ART

It is widely known that overuse of eyes through use of television, a computer, a portable terminal, and the like, which reduces blinking, and drying of air due to heating and cooling, which leads to evaporation of tears, cause dry eye symptoms. Dry eye is defined as a multifactorial disease of the tears and corneal surface that results in discomfort, visual disturbance, and tear layer instability with damage to the corneal surface (Non Patent Literature 1). An ophthalmic solution is often used for prevention, amelioration, and treatment of the dry eye symptoms. The tears may be classified into a tear aqueous layer containing water and mucin, and a tear lipid layer containing lipids and the like (Non Patent Literature 2). Basically, an approach to the tear aqueous layer is often adopted for prevention, amelioration, and treatment of the dry eye symptoms.

The approach to the tear aqueous layer has focus on the water in the tear aqueous layer, and is aimed at alleviation/amelioration of the dry eye symptoms by supplying water. This approach is a treatment method that has been heretofore widely performed as an artificial tear (Non Patent Literature 3). In addition, in recent years, there has also been known an approach with focus on the mucin in the tear aqueous layer, which is aimed at stabilizing the tear aqueous layer (uniform wetting and spreading of the tear aqueous layer over the corneal surface without rupture) by promoting mucin production. Drugs, such as Diquafosol and Rebamipide, having mucin production-promoting effects have been developed, and it has been reported that those drugs are used in dry eye treatment and have achieved high treatment effects (Non Patent Literature 4 and Non Patent Literature 5).

In recent years, it has been known that there are not a few cases of dry eye resulting from a reduction in secretion amount of the tear lipid layer due to, for example, Meibomian gland dysfunction or hypofunction (evaporative dry eye caused by Meibomian gland dysfunction) (Non Patent Literature 6). Normally, the tear lipid layer suppresses evaporation of the tear aqueous layer by covering a surface of the tear aqueous layer, to thereby prevent a dry eye condition. However, when the tear lipid layer is not secreted enough to be able to spread over the entirety of the tear aqueous layer, the tear aqueous layer cannot be protected, and hence the evaporation of the tear aqueous layer is accelerated, resulting in development of the dry eye symptoms. With regard to the evaporative dry eye, an investigation has been made into blending an oily component into an ophthalmic solution to supply the tear lipid layer from the ophthalmic solution (Patent Literature 1). As an evaluation method for an ophthalmic solution for, for example, prevention/treatment of evaporative dry eye symptoms caused by Meibomian gland dysfunction, there is known a measurement method for determining whether the tear aqueous layer and the tear lipid layer are separated into two layers (Non Patent Literature 7 and Non Patent Literature 8).

However, in development of eye drops for an evaporative dry eye application, in reality, a phenomenon in which the oily component in the eye drops is dispersed on the ocular surface, such as blurring of vision, occurs, and under the circumstances, even a dry eye treatment effect obtained by administering the eye drops containing the oily component is insufficient.

A polymer containing 2-methacryloyloxyethyl phosphorylcholine (MPC) (MPC polymer) is a polymer having extremely high hydrophilicity. The only known ophthalmological applications in which the MPC polymer is utilized are: an application as a contact lens lubricant for improving comfort of contact lens wear (Patent Literature 3); an application as an ophthalmic solution having blended therein the MPC polymer, for alleviating cytotoxicity (Patent Literature 2 and Non Patent Literature 9); and the like. No more novel applications have been provided.

As described above, under the circumstances, there has yet to be obtained a satisfactory ophthalmic solution for prevention, alleviation, amelioration, or treatment of evaporative dry eye symptoms caused by Meibomian gland dysfunction.

CITATION LIST

Patent Literature

[PTL 1] WO 2006/009112 A1
[PTL 2] WO 2015/029717 A1
[PTL 3] WO 2002/015911 A1

Non Patent Literature

[NPL 1] 2007 Report of the International Dry Eye Workshop (DEWS)
[NPL 2] Ilene K. Gipson, Distribution of mucins at the ocular surface, Experimental Eye Res., 78, 379-388, 2004.
[NPL 3] Majid Moshirfar et al., Artificial Tears Potpourri: A Literature Review, Clinical Ophthalmology, 8, 1419-1433, 2014.
[NPL 4] Gillian M. Keating, Diquafosol Ophthalmic Solution 3%: A Review of Its Use in Dry Eye, Drugs, 75, 911-922, 2015.
[NPL 5] Tomoyuki Kashima et al., Rebamipide Ophthalmic Suspension for the Treatment of Dry Eye Syndrome: A Critical Appraisal, Clinical Ophthalmology, 8, 1003-1010, 2014.
[NPL 6] G. N. Foulks, A. J. Bron, Meibomian gland dysfunction: A clinical scheme for description, diagnostics, classification, and grading., Ocul. Surf., 1, 107-126, 2003.

[NPL 7] James E. McDonalds, Surface Phenomena of Tear Film, Trans. Am. Ophthalmil. Sol, 66, 905-939, 1968.

[NPL 8] Jianhua Wang et al., Precorneal and Pre- and Postlens Tear Film Thickness Measured Indirectly with Optical Coherence Tomography, Invest. Ophth. Vis. Sci., 44, 2524-2528, 2003.

[NPL 9] Masahito Ayaki et al., Cytotoxicity assays of new artificial tears containing 2-methacryloyloxyethyl phosphorylcholine polymer for ocular surface cells, Jpn. J. Ophthalmol, 55, 541-546, 2011.

SUMMARY OF INVENTION

Technical Problem

It is an object of the present invention to provide an ophthalmic solution that is capable of stabilizing a tear lipid layer and allowing the tear lipid layer to sufficiently spread over a corneal surface, to thereby prevent the evaporation of a tear aqueous layer on the corneal surface, and hence is suitable for prevention, alleviation, amelioration, or treatment of evaporative dry eye symptoms caused by Meibomian gland dysfunction.

Solution to Problem

The inventors of the present invention have made extensive investigations in order to achieve the above-mentioned object, and as a result, have found that the object can be achieved by using, as a tear lipid layer stabilizer, a copolymer containing a constituent unit based on 2-(meth)acryloyloxyethyl phosphorylcholine and a constituent unit based on an alkyl group-containing (meth)acrylic monomer. Thus, the inventors have completed the present invention.

That is, the present invention is as described below.

[1] A tear lipid layer stabilizer, including a copolymer that has a weight-average molecular weight of from 10,000 to 5,000,000, and contains 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer:

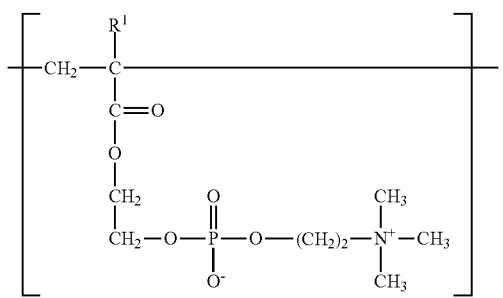

(A)

$R^1$ represents a hydrogen atom or a methyl group; and

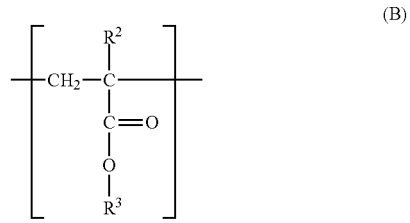

(B)

$R^2$ represents a hydrogen atom or a methyl group, and $R^3$ represents an alkyl group having 4 to 18 carbon atoms.

[2] A tear lipid layer stabilizer according to the above-mentioned item [1], wherein the constituent unit (A) includes a constituent unit based on 2-methacryloyloxyethyl phosphorylcholine, and the constituent unit (B) includes a constituent unit based on butyl methacrylate.

[3] An ophthalmic solution, including:
  0.001 w/w % to 5.0 w/w % of the tear lipid layer stabilizer of the above-mentioned item [1] or [2]; and
  water.

[4] An ophthalmic solution according to the above-mentioned item [3], further including 0.001 w/w % to 10.0 w/w % of at least one kind of thickener.

[5] An ophthalmic solution according to the above-mentioned item [4], wherein the thickener includes hydroxypropyl methylcellulose.

[6] An ophthalmic solution according to the above-mentioned item [4], wherein the thickener includes sodium hyaluronate.

[7] An ophthalmic solution according to the above-mentioned item [4], wherein the thickener includes polyvinyl alcohol.

[8] An ophthalmic solution according to the above-mentioned item [4], wherein the thickener includes polyvinylpyrrolidone.

[9] An ophthalmic solution according to any one of the above-mentioned items [3] to [8], wherein the ophthalmic solution is for use in prevention, alleviation, amelioration, or treatment of evaporative dry eye caused by Meibomian gland dysfunction.

[10] A tear lipid layer-stabilizing method, including a step of administering, to a mammal including a human, a tear lipid layer stabilizer containing a copolymer that has a weight-average molecular weight of from 10,000 to 5,000,000, and contains 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer, or an ophthalmic solution containing the stabilizer:

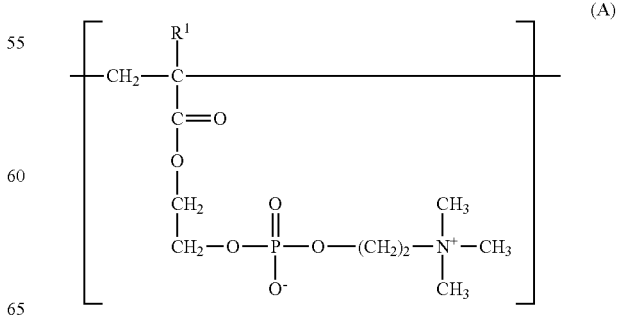

(A)

$R^1$ represents a hydrogen atom or a methyl group; and

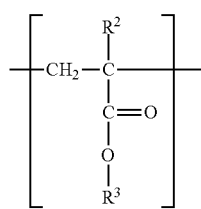

$R^2$ represents a hydrogen atom or a methyl group, and $R^3$ represents an alkyl group having 4 to 18 carbon atoms.

[11] A tear lipid layer-stabilizing method according to the above-mentioned item [10], wherein the mammal including a human includes a patient in need of prevention, alleviation, amelioration, or treatment of evaporative dry eye caused by Meibomian gland dysfunction.

[12] A copolymer for stabilizing a tear lipid layer, the copolymer having a weight-average molecular weight of from 10,000 to 5,000,000, and containing 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer:

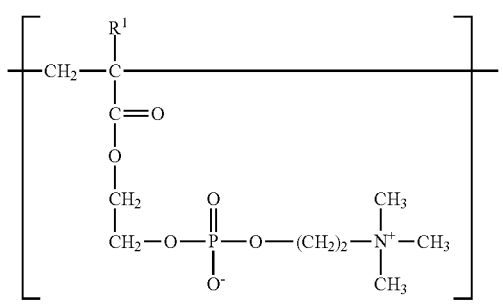

$R^1$ represents a hydrogen atom or a methyl group; and

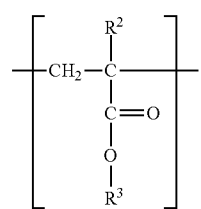

$R^2$ represents a hydrogen atom or a methyl group, and $R^3$ represents an alkyl group having 4 to 18 carbon atoms.

[13] A use of a copolymer for producing a tear lipid layer stabilizer, the copolymer having a weight-average molecular weight of from 10,000 to 5,000,000, and containing 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer:

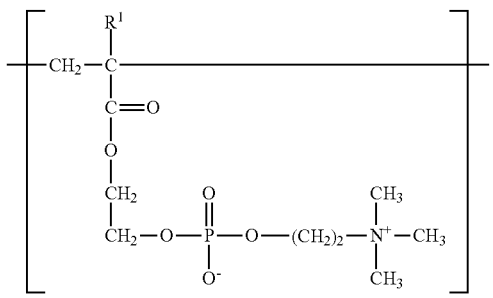

$R^1$ represents a hydrogen atom or a methyl group; and

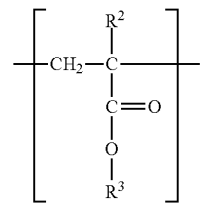

$R^2$ represents a hydrogen atom or a methyl group, and $R^3$ represents an alkyl group having 4 to 18 carbon atoms.

Advantageous Effects of Invention

The tear lipid layer stabilizer, the ophthalmic solution, and the tear lipid layer-stabilizing method of the present invention are capable of allowing a tear lipid layer to sufficiently spread over a corneal surface, to thereby prevent the evaporation of a tear aqueous layer on the corneal surface, and hence are useful for prevention, alleviation, amelioration, or treatment of evaporative dry eye symptoms caused by Meibomian gland dysfunction.

BRIEF DESCRIPTION OF DRAWINGS

FIG. 1 is a drawing including side-view photographs taken of test liquid containers used for evaluation of tear lipid layer stabilizers. The appearance of a container of Example 1-1 is shown in the left photograph, and the appearance of a container of Comparative Example 1-1 is shown in the right photograph.

DESCRIPTION OF EMBODIMENTS

The present invention is described in more detail below.

A tear lipid layer stabilizer of the present invention comprises a copolymer containing a constituent unit (A) based on 2-(meth)acryloyloxyethyl phosphorylcholine and a constituent unit (B) based on an alkyl group-containing (meth)acrylic monomer, or consists of a copolymer containing a constituent unit (A) based on 2-(meth)acryloyloxyethyl phosphorylcholine and a constituent unit (B) based on an alkyl group-containing (meth)acrylic monomer.

<Constituent Unit (A) Based on 2-(Meth)acryloyloxyethyl Phosphorylcholine>

The constituent unit (A) based on 2-(meth)acryloyloxyethyl phosphorylcholine is more specifically represented by the following formula (A), and is obtained by the polymerization of a monomer represented by the formula (A').

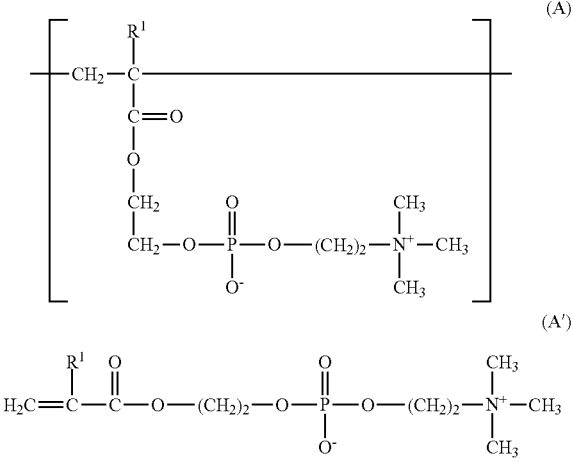

(A)

(A')

In each of the formula (A) and the formula (A'), $R^1$, which may represent any one of a hydrogen atom and a methyl group, preferably represents a methyl group. When the copolymer to be used in the present invention has the constituent unit (A) in its molecular chain, a tear lipid layer-stabilizing effect can be expressed.

The content of the constituent unit (A) in the copolymer to be used in the present invention is from 10 mol % to 90 mol %, preferably from 20 mol % to 90 mol %, more preferably from 30 mol % to 90 mol %. When the content is less than 10 mol %, the tear lipid layer-stabilizing effect cannot be expected. When the content is more than 90 mol %, the copolymer is localized in a tear aqueous layer owing to the hydrophilicity of its MPC segment to weaken an effect of allowing a tear lipid layer to spread over the tear aqueous layer, and hence the tear lipid layer-stabilizing effect is unlikely to be achieved.

A suitable example of the 2-(meth)acryloyloxyethyl phosphorylcholine is 2-methacryloyloxyethyl phosphorylcholine.

<Constituent Unit (B) Based on Alkyl Group-Containing (Meth)acrylic Monomer>

The constituent unit (B) based on the alkyl group-containing (meth)acrylic monomer is more specifically represented by the following formula (B), and is obtained by the polymerization of a monomer represented by the formula (B').

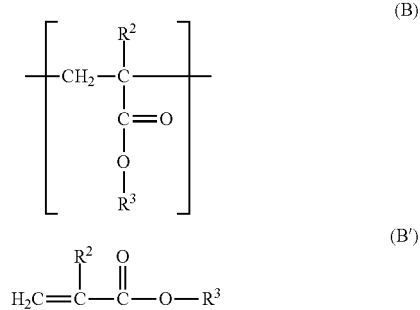

(B)

(B')

In each of the formula (B) and the formula (B'), $R^2$, which may represent any one of a hydrogen atom and a methyl group, preferably represents a methyl group, and $R^3$ may represent any one of linear and branched alkyl groups each having 4 to 18 carbon atoms.

Specific examples of the linear alkyl group having 4 to 18 carbon atoms include a n-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, and a n-octadecyl group.

Examples of the branched alkyl group having 4 to 18 carbon atoms include a t-butyl group, an isobutyl group, an isopentyl group, a t-pentyl group, a neopentyl group, an isohexyl group, an isoheptyl group, an isooctyl group, an isononyl group, an isodecyl group, an isoundecyl group, an isododecyl group, an isotridecyl group, an isotetradecyl group, an isopentadecyl group, an isohexadecyl group, an isoheptadecyl group, and an isooctadecyl group.

From the viewpoint of balance between hydrophilicity and lipophilicity of the copolymer, the linear alkyl group is preferred, and a n-butyl group, a n-dodecyl group, and a n-octadecyl group are more preferred. Further, a n-butyl group is most preferred.

Any monomer having a structure satisfying the constituent unit (B) does not disturb the balance between hydrophilicity and lipophilicity of the copolymer, and hence may be used. However, from the viewpoint of further enhancing the tear lipid layer-stabilizing effect of the copolymer, suitable examples of the alkyl group-containing (meth)acrylic monomer include butyl (meth)acrylate, lauryl (meth)acrylate, and stearyl (meth)acrylate. Further, butyl (meth)acrylate is most preferred.

By virtue of having the constituent unit (B) in the molecular chain, the copolymer to be used in the present invention enhances the lipophilicity of the copolymer, does not disturb the balance between hydrophilicity and lipophilicity, and can allow the tear lipid layer to spread over the tear aqueous layer. Accordingly, the tear lipid layer-stabilizing effect is enhanced. Further, by virtue of having the constituent unit (B) and the constituent unit (A) in the same polymer chain, the copolymer to be used in the present invention serves as a tear lipid layer stabilizer.

The content of the constituent unit (B) in the copolymer to be used in the present invention is from 10 mol % to 90 mol %, preferably from 10 mol % to 80 mol %, more preferably from 10 mol % to 70 mol %. When the content is less than 10 mol %, there is a risk in that the lipophilicity of the copolymer may be poor, disturbing the balance between hydrophilicity and lipophilicity to weaken the action of allowing the tear lipid layer to spread over the tear aqueous layer, with the result that the tear lipid layer-stabilizing effect is unlikely to be achieved. In addition, when the content is more than 90 mol %, there is a risk in that it may be difficult to produce an ophthalmic solution owing to a decrease in solubility in water.

Suitable examples of the combination of the constituent unit (A) and the constituent unit (B) contained in the molecular chain of the copolymer to be used in the present invention include the following combinations from the viewpoint of the tear lipid layer-stabilizing effect.

2-(Meth)acryloyloxyethyl phosphorylcholine (A) and butyl (meth)acrylate (B);

2-(meth)acryloyloxyethyl phosphorylcholine (A) and stearyl (meth)acrylate (B);

2-(meth)acryloyloxyethyl phosphorylcholine (A) and lauryl (meth)acrylate (B).

Although the copolymer to be used in the present invention may contain a constituent unit except the constituent unit (A) and the constituent unit (B), the copolymer is preferably formed only of the constituent unit (A) and the constituent unit (B).

An MPC polymer obtained by performing polymerization in accordance with the method of JP 11-035605 A and an MPC polymer obtained by performing polymerization in accordance with the method of JP 2004-196868 A may each be used as the copolymer to be used in the present invention.

The weight-average molecular weight of the copolymer to be used in the present invention is from 10,000 to 5,000,000, preferably from 20,000 to 1,000,000, more preferably from 50,000 to 1,000,000. When the weight-average molecular weight is less than 10,000, the lipophilicity is decreased, and hence the tear lipid layer-stabilizing effect is unlikely to be achieved. When the weight-average molecular weight is more than 5,000,000, there is a risk in that it may be difficult to produce an ophthalmic solution owing to a rapid increase in viscosity.

When the copolymer is used as a tear lipid layer stabilizer (or a component of a tear lipid layer stabilizer), the blending amount of the copolymer is from 0.001 w/w % to 5.0 w/w %, preferably from 0.005 w/w % to 5.0 w/w %, more preferably from 0.01 w/w % to 5.0 w/w % with respect to the entirety of a composition (e.g., a product or an ophthalmic solution containing the tear lipid layer stabilizer). When the blending amount is less than 0.001 w/w %, there is a risk in that the tear lipid layer-stabilizing effect may not be obtained. Even when the blending amount is more than 5.0 w/w %, an effect commensurate with the amount added is not obtained.

Further, when the copolymer is incorporated as the tear lipid layer stabilizer into the ophthalmic solution, the tear lipid layer, which contains lipids and the like, can be allowed to spread over the tear aqueous layer thinly and uniformly, to thereby express a tear lipid layer-stabilizing effect.

As a thickener to be used in the present invention, there are given a carboxyvinyl polymer, hydroxyethyl cellulose, hydroxypropyl methylcellulose, methyl cellulose, alginic acid, polyvinyl alcohol (containing both of a wholly saponified product and a partially saponified product), polyvinylpyrrolidone, polyethylene glycol, sodium chondroitin sulfate, and sodium hyaluronate. From the viewpoint of further enhancing the tear lipid layer-stabilizing effect, hydroxypropyl methylcellulose, hydroxyethyl cellulose, polyvinyl alcohol, polyvinylpyrrolidone, sodium hyaluronate, and sodium chondroitin sulfate are preferred.

When any of those thickeners is incorporated into the ophthalmic solution, the tear lipid layer can be further stabilized.

Further, the thickener can improve the retentivity of the tear lipid layer stabilizer on the ocular surface to allow the tear lipid layer-stabilizing effect to persist.

The content of the thickener in the present invention only needs to be generally from 0.001 w/w % to 10.0 w/w %. From the viewpoint of further enhancing the tear lipid layer-stabilizing effect, the content is preferably from 0.002 w/w % to 9.5 w/w %, more preferably from 0.003 w/w % to 9.0 w/w %, still more preferably from 0.01 w/w % to 9.0 w/w %. More specifically, the content of the thickener is as described below.

The content of the carboxyvinyl polymer in the present invention only needs to be generally from 0.001 w/w % to 10.0 w/w %. From the viewpoint of further enhancing the tear lipid layer-stabilizing effect, the content is preferably from 0.002 w/w % to 9.5 w/w %, more preferably from 0.003 w/w % to 9.0 w/w %, still more preferably from 0.01 w/w % to 9.0 w/w %.

The content of hydroxyethyl cellulose in the present invention only needs to be generally from 0.001 w/w % to 5.0 w/w %. From the viewpoint of further enhancing the tear lipid layer-stabilizing effect, the content is preferably from 0.003 w/w % to 5.0 w/w %, more preferably from 0.005 w/w % to 3.0 w/w %, still more preferably from 0.01 w/w % to 2.0 w/w %.

The content of hydroxypropyl methylcellulose in the present invention only needs to be generally from 0.001 w/w % to 5.0 w/w %. From the viewpoint of further enhancing the tear lipid layer-stabilizing effect, the content is preferably from 0.003 w/w % to 5.0 w/w %, more preferably from 0.005 w/w % to 3.0 w/w %, still more preferably from 0.01 w/w % to 2.0 w/w %.

The content of methyl cellulose in the present invention only needs to be generally from 0.001 w/w % to 5.0 w/w %. From the viewpoint of further enhancing the tear lipid layer-stabilizing effect, the content is preferably from 0.003 w/w % to 5.0 w/w %, more preferably from 0.005 w/w % to 3.0 w/w %, still more preferably from 0.01 w/w % to 2.0 w/w %.

The content of alginic acid in the present invention only needs to be generally from 0.001 w/w % to 10.0 w/w %. From the viewpoint of further enhancing the tear lipid layer-stabilizing effect, the content is preferably from 0.002 w/w % to 9.5 w/w %, more preferably from 0.003 w/w % to 9.0 w/w %, still more preferably from 0.01 w/w % to 9.0 w/w %.

The content of polyvinyl alcohol in the present invention only needs to be generally from 0.001 w/w % to 10.0 w/w %. From the viewpoint of further enhancing the tear lipid layer-stabilizing effect, the content is preferably from 0.002 w/w % to 9.5 w/w %, more preferably from 0.003 w/w % to 9.0 w/w %, still more preferably from 0.01 w/w % to 9.0 w/w %.

The content of polyvinylpyrrolidone in the present invention only needs to be generally from 0.001 w/w % to 10.0 w/w %. From the viewpoint of further enhancing the tear lipid layer-stabilizing effect, the content is preferably from 0.002 w/w % to 9.5 w/w %, more preferably from 0.003 w/w % to 9.0 w/w %, still more preferably from 0.01 w/w % to 9.0 w/w %.

The content of polyethylene glycol in the present invention only needs to be generally from 0.001 w/w % to 10.0 w/w %. From the viewpoint of further enhancing the tear lipid layer-stabilizing effect, the content is preferably from 0.002 w/w % to 9.5 w/w %, more preferably from 0.003 w/w % to 9.0 w/w %, still more preferably from 0.01 w/w % to 9.0 w/w %.

The content of sodium chondroitin sulfate in the present invention only needs to be generally from 0.001 w/w % to 5.0 w/w %. From the viewpoint of further enhancing the tear lipid layer-stabilizing effect, the content is preferably from 0.003 w/w % to 5.0 w/w %, more preferably from 0.005 w/w % to 3.0 w/w %, still more preferably from 0.01 w/w % to 2.0 w/w %.

The content of sodium hyaluronate in the present invention only needs to be generally from 0.001 w/w % to 5.0 w/w %. From the viewpoint of further enhancing the tear lipid layer-stabilizing effect, the content is preferably from 0.003 w/w % to 5.0 w/w %, more preferably from 0.005 w/w % to 3.0 w/w %, still more preferably from 0.01 w/w % to 2.0 w/w %.

In the tear lipid layer stabilizer or the ophthalmic solution of the present invention, in addition to the copolymer and the thickener, a decongestant component, an anti-inflammatory and astringent component, a vitamin, an amino acid, a sulfa drug, a saccharide, a cooling agent, an inorganic salt, an organic acid salt, an acid, a base, an antioxidant, a stabilizer, an antiseptic, a mucin secretagogue, or the like that may be generally used for an ophthalmic solution may be blended as required.

Examples of the decongestant component include epinephrine or salts thereof, ephedrine hydrochloride, tetrahydrozoline hydrochloride, naphazoline or salts thereof, phenylephrine, and methylephedrine hydrochloride.

Examples of the anti-inflammatory and astringent component include ε-aminocaproic acid, allantoin, berberine or salts thereof, sodium azulene sulfonate, glycyrrhizic acid or salts thereof, zinc lactate, zinc sulfate, and lysozyme chloride.

Examples of the vitamin include sodium flavin adenine dinucleotide, cyanocobalamin, retinol acetate, retinol palmitate, pyridoxine hydrochloride, panthenol, sodium pantothenate, and calcium pantothenate.

Examples of the amino acid include aspartic acid or salts thereof, and aminoethylsulfonic acid.

Examples of the sulfa drug include sulfamethoxazole or salts thereof, sulfisoxazole, and sodium sulfisomidine.

Examples of the saccharide include glucose, mannitol, sorbitol, xylitol, and trehalose.

Examples of the cooling agent include menthol and camphor.

Examples of the inorganic salt include sodium chloride, potassium chloride, borax, sodium hydrogen carbonate, sodium hydrogen phosphate, and anhydrous sodium dihydrogen phosphate.

An example of the organic acid salt is sodium citrate.

Examples of the acid include boric acid, phosphoric acid, citric acid, sulfuric acid, acetic acid, and hydrochloric acid.

Examples of the base include sodium hydroxide, potassium hydroxide, trishydroxymethylaminomethane, and monoethanolamine.

Examples of the antioxidant include tocopherol acetate and dibutylhydroxytoluene.

Examples of the stabilizer include sodium edetate and glycine.

Examples of the antiseptic include benzalkonium chloride, chlorhexidine gluconate, potassium sorbate, methylparaben, ethylparaben, propylparaben, isopropylparaben, butylparaben, isobutylparaben, and polyhexanide hydrochloride.

Examples of the mucin secretagogue include diquafosol sodium and rebamipide.

Water to be used in the present invention is preferably pure water, purified water, ion-exchanged water, or the like from the standpoint of safety.

A specific form of a product including the tear lipid layer stabilizer of the present invention may be exemplified by the following: medical eye drops, general eye drops, antibiotic eye drops, eyewashes, contact lens wetting solutions, artificial tears, and the like.

A production method for the ophthalmic solution of the present invention is described.

The ophthalmic solution of the present invention may be produced by adding the copolymer (tear lipid layer stabilizer) of the present invention, and as desired, the thickener to be used in the present invention and/or the above-mentioned components that may be generally used for ophthalmic solutions, into water at from room temperature to about 80° C., and stirring the mixture to dissolution. In addition, with regard to the order in which the copolymer, the thickener, and the components that may be generally used for ophthalmic solutions are added, any one of the components may be added first.

With regard to heating, cooling, and stirring in the production, it is only necessary that the entire solution can be uniformly heated, cooled, and stirred. The heating, the cooling, and the stirring may each be performed by using a known instrument or apparatus.

The present invention is also directed to a tear lipid layer-stabilizing method including the following step.

A step of administering, to a mammal including a human, a tear lipid layer stabilizer containing a copolymer that has a weight-average molecular weight of from 10,000 to 5,000,000, and contains 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer, or an ophthalmic solution containing the stabilizer:

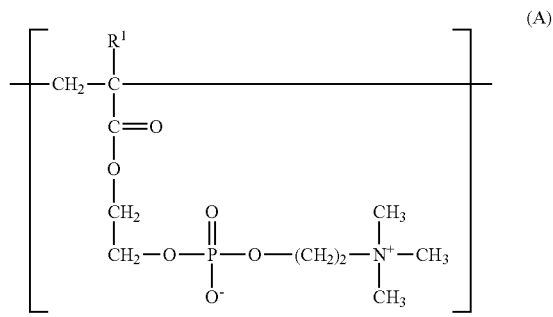

$R^1$ represents a hydrogen atom or a methyl group; and

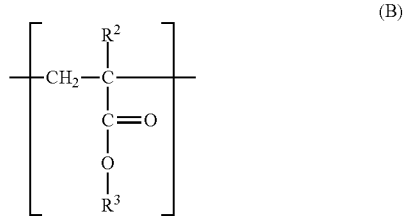

$R^2$ represents a hydrogen atom or a methyl group, and $R^3$ represents an alkyl group having 4 to 18 carbon atoms.

The tear lipid layer-stabilizing method of the present invention is not particularly limited, but may include, for example, dropping 0.01 mL to 0.2 mL of the tear lipid layer stabilizer of the present invention or the ophthalmic solution of the present invention to an eye (eyeball) from any angle 1 to 10 times, 1 to 8 times, 1 to 6 times, 1 to 4 times, or 1 to 3 times a day (preferably in the morning, the afternoon, and the evening).

A target of the tear lipid layer-stabilizing method, which is not particularly limited, is a mammal including a human, and the target is preferably a patient in need of prevention, alleviation, amelioration, or treatment of evaporative dry eye caused by Meibomian gland dysfunction.

The present invention is also directed to a copolymer for stabilizing a tear lipid layer, the copolymer having a weight-average molecular weight of from 10,000 to 5,000,000, and containing 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer:

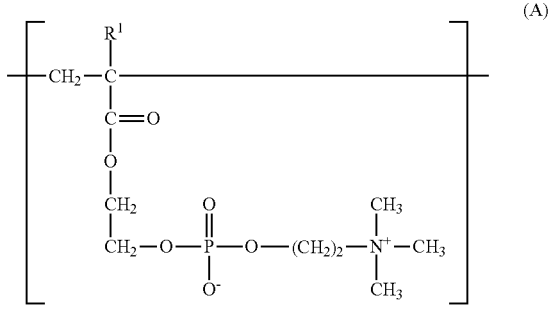

$R^1$ represents a hydrogen atom or a methyl group; and

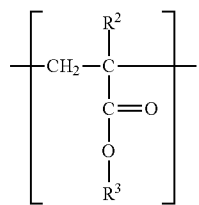

$R^2$ represents a hydrogen atom or a methyl group, and $R^3$ represents an alkyl group having 4 to 18 carbon atoms.

The present invention is also directed to a use of a copolymer for producing a tear lipid layer stabilizer, the copolymer having a weight-average molecular weight of from 10,000 to 5,000,000, and containing 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer:

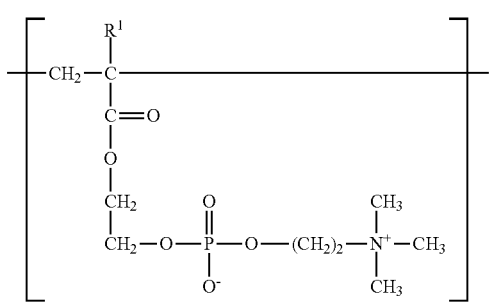

$R^1$ represents a hydrogen atom or a methyl group; and

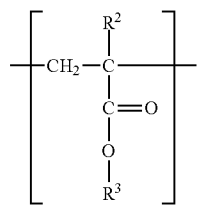

$R^2$ represents a hydrogen atom or a methyl group, and $R^3$ represents an alkyl group having 4 to 18 carbon atoms.

EXAMPLES

The present invention and its effects are specifically described by way of the following Examples and Comparative Examples.

Copolymers used in Examples and Comparative Examples are as described below.

MPC polymer (1): A 2-methacryloyloxyethyl phosphorylcholine (A)-butyl methacrylate (B) copolymer [copolymerization composition ratio (molar ratio): 80/20, weight-average molecular weight: 600,000] obtained by performing polymerization in conformity with a method described in Examples of JP 11-035605 A.

MPC polymer (2): A 2-methacryloyloxyethyl phosphorylcholine (A)-butyl methacrylate (B) copolymer [copolymerization composition ratio (molar ratio): 30/70, weight-average molecular weight: 142,000] obtained by performing polymerization in conformity with a method described in Examples of JP 2004-196868 A.

<Tear Lipid Layer Stabilization Evaluation>

With regard to a tear on an ocular surface, under a state in which the tear lipid layer is present without rupture and distributed over the tear aqueous layer, the tear lipid layer covers the tear aqueous layer, and hence can suppress the evaporation of water to alleviate dry eye symptoms. In addition, when the tear aqueous layer and the tear lipid layer mix with each other to be brought into a clouded/dispersed state as a whole, blurring of vision may occur. In this case, even if produced, an ophthalmic solution cannot be utilized (reference: Literature 1). In view of the foregoing, a procedure for reproducing and evaluating a state under which dry eye symptoms could be alleviated was set with reference to Literature 2 and Literature 3. For the evaluation, the following artificial eye discharge was prepared in advance, and tear lipid layer stabilization evaluation was performed in accordance with the evaluation procedure.

The tear lipid layer-stabilizing effect in the present invention refers to an effect of preventing the evaporation of the tear aqueous layer on the corneal surface by allowing the tear lipid layer to be sufficiently distributed over the tear aqueous layer on the corneal surface without rupture. More concisely, the tear lipid layer-stabilizing effect refers to an effect of preventing the evaporation of the tear aqueous layer on the corneal surface by allowing the tear lipid layer to sufficiently spread over the corneal surface.

[Preparation of Artificial Eye Discharge]

(1) 1.813 g of phosphoric acid and 0.9585 g of boric acid were weighed out, and water was added to provide a phosphate-borate buffer having a volume of 500 mL.

(2) 0.06 g of oleic acid, 0.06 g of linolenic acid, 0.81 g of tripalmitin, 0.20 g of cetyl alcohol, 0.06 g of palmitic acid, 0.81 g of spermaceti, 0.06 g of cholesterol, 0.08 g of cholesteryl palmitate, and 2.83 g of lecithin (of egg origin) were added to 100 mL of the phosphate-borate buffer in a beaker.

(3) The phosphate-borate buffer after the (2) was suspended so as to become uniform using a mixer, and the resultant was used as an artificial eye discharge.

[Evaluation Procedure]

With reference to Literature 2 and Literature 3 below, in view of the fact that tears have an oil content of about 3%, the evaluation procedure was set as described in the following (1) to (3).

(1) 10 mL of a solution of Example or Comparative Example (assumed to be a tear aqueous layer having added thereto a tear lipid layer stabilizer) was put into a glass Petri dish having a diameter of 40 mm.

(2) Further, 0.25 mL of the artificial eye discharge (assumed to be a tear lipid layer) was added.

(3) Immediately after the addition of the solution of Example or Comparative Example and the artificial eye discharge to the glass Petri dish, layer separability and persistence were evaluated in accordance with the following evaluation criteria.

<Evaluation Criteria (Layer Separability)>

+++: Two layers are separated from each other.

++: Clouding/dispersion is slightly observed, but two layers are separated from each other (usable as an ophthalmic solution).

+: Clouding/dispersion is partially observed, but two layers are separated from each other (usable as an ophthalmic solution).

−: Clouding/dispersion occurs.

<Evaluation Criteria (Persistence)>

A period of time for which two layers were separated from each other was measured, and the persistence of a tear lipid layer-stabilizing effect was evaluated.

Literature 1: Michael A. Lamp et al., Distribution of Aqueous-Deficient and Evaporative Dry Eye in a Clinic-Based Patient Cohort: A Retrospective Study, Cornea, 31, 472-478, 2012.

Literature 2: James E. McDonalds, Surface Phenomena of Tear Film, Trans. Am. Ophthalmol. Soc., 66, 905-939, 1968.

Literature 3: Jianhua Wang et al., Precorneal and Pre- and Postlens Tear Film Thickness Measured Indirectly with Optical Coherence Tomography, Invest. Ophth. Vis. Sci., 44, 2524-2528, 2003.

Example 1-1

5 g of the MPC polymer (1) was weighed out, and 95 g of purified water was added thereto and mixed therewith by stirring to completely dissolve the polymer. The solution was defined as Example 1-1. The details thereof are shown in Table 1 below.

Example 1-2 to Example 1-6 and Comparative Example 1-1

Solutions were produced in accordance with the same procedure as in Example 1-1 except that components whose kinds and amounts were shown in Table 1 were used. The solutions were respectively defined as Example 1-2 to Example 1-6 and Comparative Example 1-1.

The tear lipid layer stabilization evaluation was performed for Example 1-1 to Example 1-6 and Comparative Example 1-1. As a result, as shown in FIG. 1, in Comparative Example 1-1, a clouded/dispersed state (evaluation result of layer separability: −, evaluation result of persistence: 0 seconds) was exhibited, and hence no tear lipid layer-stabilizing effect was observed. Meanwhile, in Example 1-1, a lipid layer was present on an aqueous layer, i.e., two layers were separated from each other (evaluation result of layer separability: +++, evaluation result of persistence: 19 seconds), and hence a tear lipid layer-stabilizing effect was achieved. In each of Example 1-2 to Example 1-5, as in Example 1-1, a tear lipid layer-stabilizing effect was found (evaluation results of layer separability: + to +++, evaluation results of persistence: 7 seconds to 16 seconds). In addition, also in Example 1-6, in which the MPC polymer (1) was changed to the MPC polymer (2), two layers were separated from each other (evaluation result of layer separability: +, evaluation result of persistence: 18 seconds), and hence a tear lipid layer-stabilizing effect was achieved.

Example 2-1

About 80 g of purified water was weighed out and heated to 80° C., and 0.1 g of hydroxypropyl methylcellulose (METOLOSE 60SH-50, manufactured by Shin-Etsu Chemical Co., Ltd.) was added thereto and mixed therewith by stirring to be dispersed therein. The dispersion was cooled to room temperature, and then 0.1 g of the MPC polymer (1) was added thereto and mixed therewith by stirring to be completely dissolved therein. The solution was defined as Example 2-1. The details thereof are shown in Table 2.

Example 2-2 to Example 2-8

Solutions were produced in accordance with the same procedure as in Example 2-1 except that components whose kinds and amounts were shown in Table 2 were used. The solutions were respectively defined as Example 2-2 to Example 2-8.

In Example 2-1 to Example 2-8, in which the MPC polymer was used in combination with various thickeners, tear lipid layer stabilization evaluation was performed by the same method as in Example 1-1.

As a result, it was revealed that two layers were separated from each other (evaluation results of layer separability: + to +++), and hence tear lipid layer-stabilizing effects were achieved.

The results revealed that the MPC polymer contributed to stabilizing the tear lipid layer, and the ophthalmic solution of the present invention that further included the thickener, such as hydroxypropyl methylcellulose, sodium hyaluronate, polyvinyl alcohol, or polyvinylpyrrolidone, also expressed a tear lipid layer-stabilizing effect.

Further, in Example 2-7, although the content of the MPC polymer (1) was lower than those of Example 1-1 to Example 1-5, the evaluation result of layer separability was +++.

In addition, with regard to the evaluation results of persistence, in each of Example 2-1 to Example 2-8 (evaluation results of persistence: 12 seconds or more (longer than 30 seconds in Example 2-7)), although the content of the MPC polymer (1) was lower than that of Example 1-5 (evaluation result of persistence: 7 seconds), the tear lipid layer-stabilizing effect persisted longer.

Those results revealed that, even when the polymer content was low, a high tear lipid layer-stabilizing effect was obtained by incorporating the thickener. That is, the thickener can enhance the tear lipid layer-stabilizing effect.

The results of Examples 1 and 2 described above revealed that the tear lipid layer stabilizer, the ophthalmic solution, and the tear lipid layer-stabilizing method of the present invention had a satisfactory tear lipid layer-stabilizing effect, and further, were suitably used for prevention, alleviation, amelioration, or treatment of evaporative dry eye symptoms caused by Meibomian gland dysfunction. Further, when the thickener was blended into the ophthalmic solution of the present invention, the tear lipid layer-stabilizing effect was able to be enhanced from the viewpoints of layer separability and persistence.

TABLE 1

|  |  |  | Example 1-1 | Example 1-2 | Example 1-3 | Example 1-4 | Example 1-5 | Example 1-6 | Comparative Example 1-1 |
|---|---|---|---|---|---|---|---|---|---|
| Composition of ophthalmic solution (w/w %) | Tear lipid layer stabilizer | MPC polymer (1) | 5.00 | 4.00 | 3.00 | 2.00 | 1.00 | | |
| | | MPC polymer (2) | | | | | | 5.00 | |
| | Water | (Purified water) | 95.00 | 96.00 | 97.00 | 98.00 | 99.00 | 95.00 | 100.00 |
| | | Total | 100.00 | 100.00 | 100.00 | 100.00 | 100.00 | 100.00 | 100.00 |
| Tear lipid layer-stabilizing effect | | Layer separability | +++ | +++ | ++ | ++ | + | + | − |
| | | Persistence (unit: seconds) | 19 | 16 | 13 | 10 | 7 | 18 | 0 |

TABLE 2

|  |  |  | Example 2-1 | Example 2-2 | Example 2-3 | Example 2-4 | Example 2-5 | Example 2-6 | Example 2-7 | Example 2-8 |
|---|---|---|---|---|---|---|---|---|---|---|
| Composition of ophthalmic solution (w/w %) | Tear lipid layer stabilizer | MPC polymer (1) | 0.10 | 0.10 | 0.10 | 0.10 | 0.10 | 0.10 | 0.50 | 0.01 |
| | | MPC polymer (2) | | | | | | | | |
| | Thickener | Hydroxypropyl methylcellulose (1) | 0.10 | | | | | | | |
| | | Hydroxypropyl methylcellulose (2) | | 0.10 | | | | | | |
| | | Sodium hyaluronate | | | 0.30 | | | | 0.30 | 0.30 |
| | | Polyvinyl alcohol | | | | 1.00 | 2.00 | | | |
| | | Polyvinylpyrrolidone | | | | | | 1.00 | | |
| | Water | (Purified water) | 99.80 | 99.80 | 99.60 | 98.90 | 97.90 | 98.90 | 99.20 | 99.69 |
| | | Total | 100.00 | 100.00 | 100.00 | 100.00 | 100.00 | 100.00 | 100.00 | 100.00 |
| Tear lipid layer-stabilizing effect | | Layer separability | ++ | ++ | ++ | ++ | ++ | ++ | +++ | + |
| | | Persistence (unit: seconds) | 21 | 23 | 26 | 16 | 19 | 14 | >30 | 12 |

The details of the materials simplified in Table 2 are as described below.

Hydroxypropyl methylcellulose (1): METOLOSE 60SH-50, manufactured by Shin-Etsu Chemical Co., Ltd.

Hydroxypropyl methylcellulose (2): METOLOSE 60SH-4000, manufactured by Shin-Etsu Chemical Co., Ltd.

Sodium hyaluronate: manufactured by Sigma-Aldrich

Polyvinyl alcohol: GOHSENOL EG-40, manufactured by The Nippon Synthetic Chemical Industry Co., Ltd.

Polyvinylpyrrolidone: Polyvinylpyrrolidone K-90, manufactured by Wako Pure Chemical Industries, Ltd.

INDUSTRIAL APPLICABILITY

The tear lipid layer stabilizer capable of achieving the stabilization of the tear lipid layer, the ophthalmic solution having blended therein the tear lipid layer stabilizer, and the tear lipid layer-stabilizing method using the tear lipid layer stabilizer can be provided. Further, the tear lipid layer stabilizer and the ophthalmic solution containing the tear lipid layer stabilizer provided by the present invention are capable of allowing the tear lipid layer to sufficiently spread over the tear aqueous layer, to thereby prevent the evaporation of the tear aqueous layer on the corneal surface, and further, are useful for prevention, alleviation, amelioration, or treatment of evaporative dry eye caused by Meibomian gland dysfunction.

The invention claimed is:

1. A method of effecting tear lipid layer stabilization on a corneal surface of a mammal:

administering, to a mammal, a tear lipid layer stabilizer containing a copolymer that has a weight-average molecular weight of from 10,000 to 5,000,000, and contains 10 mol % to 90 mol % of a constituent unit (A) based on 2-(meth)acryloyloxyethyl phosphorylcholine and 90 mol % to 10 mol % of a constituent unit (B) based on an alkyl group-containing (meth)acrylic monomer, or an ophthalmic solution containing the stabilizer:

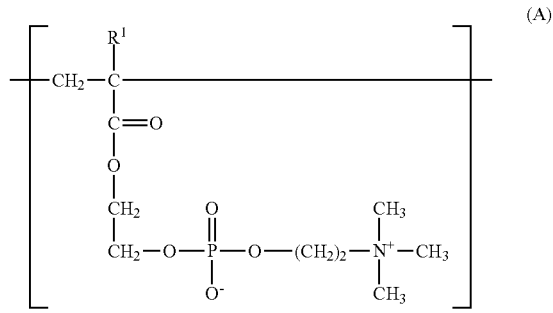

$R^1$ represents a hydrogen atom or a methyl group; and

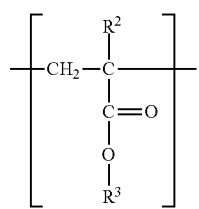 (B)

R² represents a hydrogen atom or a methyl group, and R³ represents an alkyl group having 4 to 18 carbon atoms in an amount effective to reduce evaporation of a tear aqueous layer, wherein the ophthalmic solution does not contain hydroxypropyl methylcellulose.

2. A tear lipid layer-stabilizing method according to claim 1, wherein the constituent unit (A) comprises a constituent unit based on 2-methacryloyloxyethyl phosphorylcholine, and the constituent unit (B) comprises a constituent unit based on butyl methacrylate.

3. A tear lipid layer-stabilizing method according to claim 2, wherein the ophthalmic solution comprises 0.001 w/w % to 10.0 w/w % of at least one kind of thickener.

4. A tear lipid layer-stabilizing method according to claim 3, wherein the thickener comprises sodium hyaluronate.

5. A tear lipid layer-stabilizing method according to claim 3, wherein the thickener comprises polyvinyl alcohol.

6. A tear lipid layer-stabilizing method according to claim 3, wherein the thickener comprises polyvinylpyrrolidone.

7. A tear lipid layer-stabilizing method according to claim 1, wherein the mammal including a human is in need of prevention, alleviation, amelioration, or treatment of evaporative dry eye caused by Meibomian gland dysfunction.

8. The method of claim 1, wherein the mammal is a human.

* * * * *